United States Patent
Okumura (10) Patent No.: US 9,513,271 B2
(45) Date of Patent: Dec. 6, 2016

(54) MOISTURE MEASURING APPARATUS AND COMPUTER-READABLE MEDIUM

(71) Applicant: CASIO COMPUTER CO., LTD., Shibuya-ku, Tokyo (JP)

(72) Inventor: Ryo Okumura, Fussa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 782 days.

(21) Appl. No.: 13/928,184

(22) Filed: Jun. 26, 2013

(65) Prior Publication Data

US 2014/0025300 A1 Jan. 23, 2014

(30) Foreign Application Priority Data

Jul. 20, 2012 (JP) ................................. 2012-161409

(51) Int. Cl.
| | |
|---|---|
| *G01V 3/00* | (2006.01) |
| *G01N 27/00* | (2006.01) |
| *G01R 27/08* | (2006.01) |
| *G01N 33/24* | (2006.01) |
| *G01N 27/04* | (2006.01) |

(52) U.S. Cl.
CPC .......... *G01N 33/246* (2013.01); *G01N 27/048* (2013.01)

(58) Field of Classification Search
CPC ... G01N 33/246; G01N 27/048; G01N 27/223
USPC ..................................... 702/2; 324/71.1, 694
See application file for complete search history.

(56) References Cited

U.S. PATENT DOCUMENTS 7,183,779 B2 * 2/2007 Hughes ................ G01N 33/246
324/664

FOREIGN PATENT DOCUMENTS

| JP | 04134060 U | 12/1992 |
|---|---|---|
| JP | 07-190974 A | 7/1995 |
| JP | 2608679 B2 | 5/1997 |
| JP | 2003265056 A | 9/2003 |

OTHER PUBLICATIONS

Japanese Office Action (and English translation thereof) dated Jun. 30, 2016, issued in Japanese Application No. 2012-161409.

* cited by examiner

*Primary Examiner* — An Do
(74) *Attorney, Agent, or Firm* — Holtz, Holtz & Volek PC (57) ABSTRACT

An object of the present invention is to provide a moisture measuring apparatus which, when the body of the apparatus for measuring a state of moisture in a measurement target object is mounted into the measurement target object, provides a user with a mounting state as to whether the moisture measuring apparatus has been appropriately mounted. In the present invention, the CPU of a moisture measuring apparatus determines the mounting state of the moisture measuring apparatus in soil that is a measurement target object (judges whether or not there is a gap between a sensor electrode and soil) based on the state of moisture (moisture amount) measured by a soil moisture amount sensor, and informs a result of the judgment.

11 Claims, 6 Drawing Sheets

TEMPERATURE TABLE — T1

| TEMPERATURE | JUDGMENT THRESHOLD VALUE | JUDGMENT TIME |
|---|---|---|
| TH | LOW SETTING | SHORT SETTING |
| Tth | STANDARD VALUE | STANDARD VALUE |
| TL | HIGH SETTING | LONG SETTING |

FIG. 3B

HUMIDITY TABLE — T2

| HUMIDITY | JUDGMENT THRESHOLD VALUE | JUDGMENT TIME |
|---|---|---|
| HH | HIGH SETTING | LONG SETTING |
| Hth | STANDARD VALUE | STANDARD VALUE |
| HL | LOW SETTING | SHORT SETTING |

FIG. 3C

SOIL TABLE — T3

| SOIL CLASSIFICATION | JUDGMENT THRESHOLD VALUE | JUDGMENT TIME |
|---|---|---|
| BLACK SOIL | STANDARD VALUE | STANDARD VALUE |
| SAND | LOW SETTING | SHORT SETTING |
| EARTH FOR FOLIAGE PLANTS | MUCH MORE LOWER SETTING | MUCH MORE SHORTER SETTING |

MAGNITUDE OF PARTICLES ⇩ LARGE

MOISTURE MEASURING APPARATUS AND COMPUTER-READABLE MEDIUM

CROSS-REFERENCE TO RELATED APPLICATION

This application is based upon and claims the benefit of priority from the prior Japanese Patent Application No. 2012-161409, filed Jul. 20, 2012, the entire contents of which are incorporated herein by reference.

BACKGROUND OF THE INVENTION

1. Field of the Invention

The present invention relates to a moisture measuring apparatus and a computer-readable medium for measuring a state of moisture in a measurement target object such as soil.

2. Description of the Related Art

Generally, soil moisture measuring apparatuses developed for farm work or kitchen gardens measure moisture included in soil based on, for example, an electric resistance method. Conventionally, there has been known a measuring apparatus having a simplified configuration in which two measuring electrodes are provided on the external surface of the body of the apparatus, as a soil moisture measuring apparatus which is thrust into soil for use and has been developed for the nurturing assistance of foliage plants and the like (See Japanese Patent No. 2608679).

However, in the aforementioned technology (the soil moisture measuring apparatus having a simplified configuration) it is ideal that the whole of the two measuring electrodes provided on the external surface of the body of the apparatus is brought into contact with soil. However, when the measuring apparatus is thrust into soil, or its position is transferred, there occurs a gap between the soil and the measuring apparatus. Accordingly, there is a problem in that the gap causes a substantial reduction in a contact area between the measuring apparatus and the soil, which impedes exact measurements.

SUMMARY OF THE INVENTION

An object of the present invention is to provide a moisture measuring apparatus which can provide a user with a mounting state as to whether the moisture measuring apparatus has been appropriately mounted, when the body of the apparatus for measuring a state of moisture in a measurement target object is mounted into the measurement target object.

In order to solve the aforementioned problems in accordance with one aspect of the present invention, there is provided a moisture measuring apparatus comprising: a moisture measuring section which measures a state of moisture in a measurement target object; a determination section which determines a mounting state of the moisture measuring apparatus in the measurement target object based on the state of moisture measured by the moisture measuring section; and an informing section which informs a result of determination by the determination section.

According to one aspect of the present invention, when the body of the apparatus for measuring a state of moisture in the measurement target object is mounted into the measurement target object, the mounting state as to whether the moisture measuring apparatus has been appropriately mounted can be provided for the user, whereby the exact measurement can be expected.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

Figures 1A, 1B:
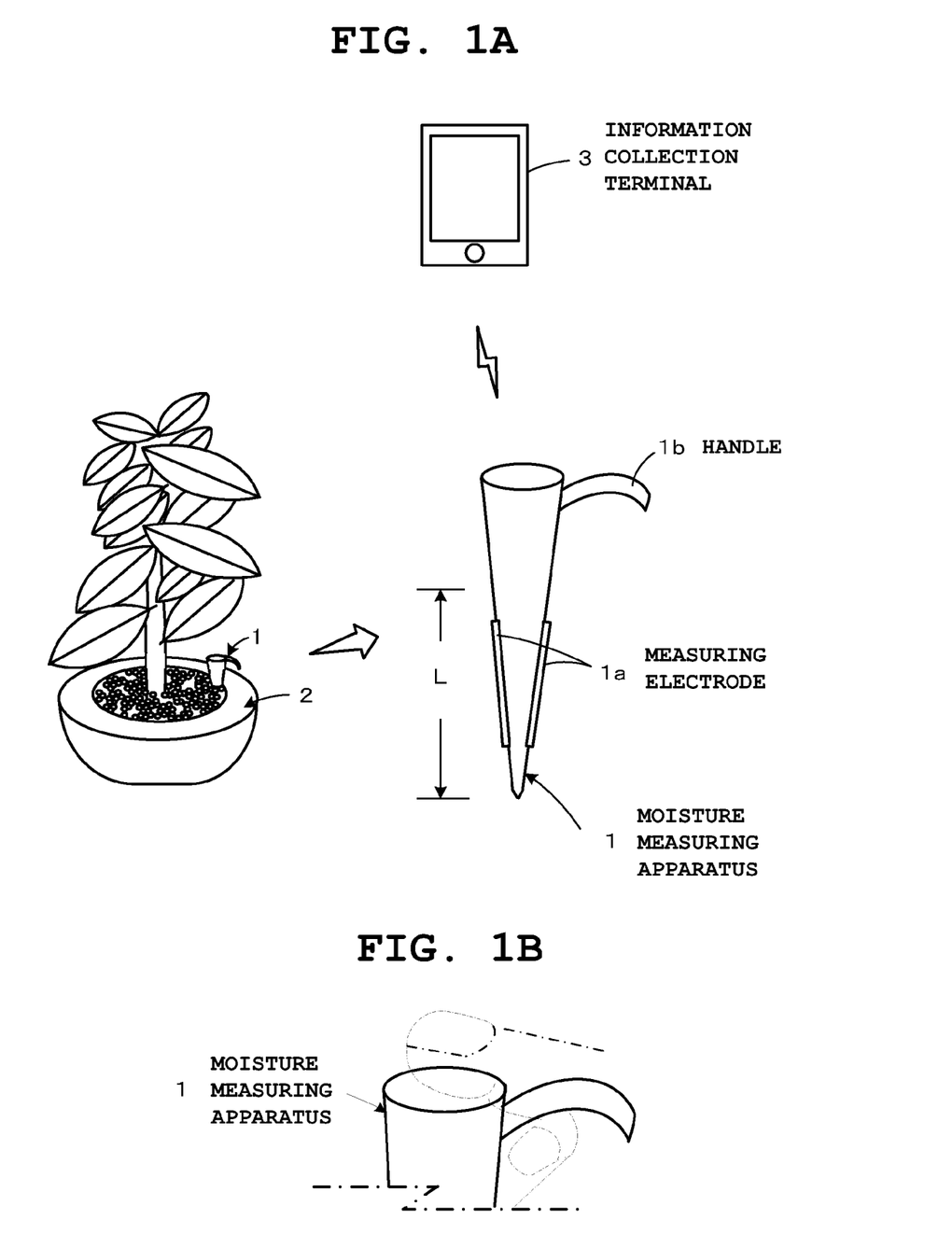
FIGS. 1A and 1B are diagrams to describe a moisture measuring apparatus which measures the amount of moisture in soil (measurement target object), as a measuring apparatus which measures the nurturing environment of plants.

Hereinafter, the embodiment of the present invention will be described referring to FIGS. 1 to 6. FIG. 1 is a diagram to describe a moisture measuring apparatus which measures the amount of moisture in soil (measurement target object), as a measuring apparatus which measures the nurturing environment of plants. The moisture measuring apparatus 1 is a plant nurturing environment measuring apparatus of a simplified configuration in which the nurturing environment (state of moisture in soil) of plants such as planted trees and flowering plants is measured based on an electric resistance method. The entire case thereof (body of apparatus) is made up of a long and narrow hollow rod body having a tapered shape. As illustrated in FIG. 1A, the rod body is structured to be buried into soil in a such a manner that the lower side portion of the case thereof that is, approximately a lower half on the side of the tip end portion is thrust into the soil (measurement target object) illustrated by the reference numeral 2.

Also, as illustrated in FIG. 1A, two plate-shaped sensor electrodes 1a which are made of materials such as copper are arranged separately from each other on the surface on the lower portion side of the case (body of apparatus). The moisture measuring apparatus 1 measures the amount of moisture in soil (measurement target object) based on an electric resistance value between the two sensor electrodes 1a. In the diagram, reference numeral L represents a range where the moisture measuring apparatus 1 is buried into the soil. A user thrusts the moisture measuring apparatus 1 into the soil in such a manner that the two sensor electrodes 1a are completely buried thereinto. Also, an arc-shaped handle 1b is projectingly formed (integrally molded) on the upper end one-side portion of the case.

As soil in a flower pot 2, generally, black soil which relatively has high moisture holding ability is often used. Needless to say, the soil is not limited to the black soil in view of the types of plants. The moisture measuring apparatus 1 transmits and receives measurement data (sensor data) between an information collection terminal 3 and the moisture measuring apparatus 1 based on general-purpose communication such as wireless LAN (Local Area Network). The information collection terminal 3 is, for example, a multifunctional portable cellular phone apparatus, which is referred to as a PC (personal computer) or a smart phone owned by the user. In a case where the moisture measuring apparatus 1 is taken out from or put in the soil in the flower pot 2, as illustrated in FIG. 1B, the take-out or put-in can smoothly be carried out by pressing the upper end surface of the moisture measuring apparatus 1 with the thick of the thumb while hooking the index finger on the lower side of the handle 1b.

Figure 2:
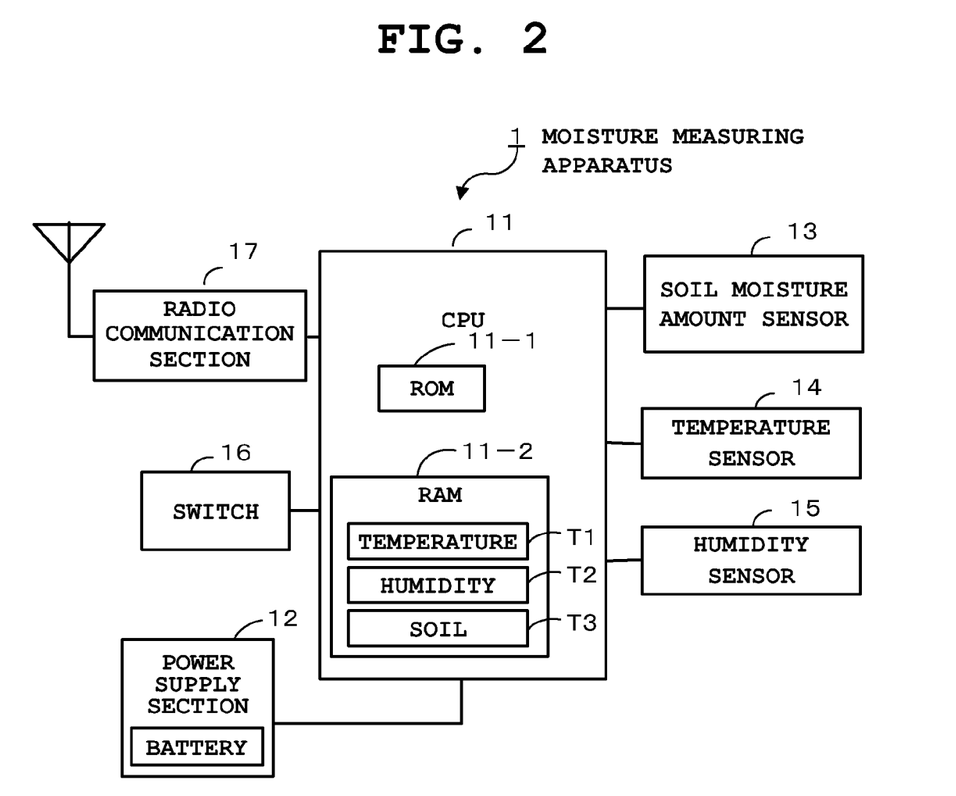
FIG. 2 is a block diagram illustrating basic components of the moisture measuring apparatus 1.

FIG. 2 is a block diagram illustrating basic components of the moisture measuring apparatus 1. A CPU 11 in FIG. 2, which is operated based on the power supplied from a power supply section 12, includes a ROM 11-1 which stores the control program and a RAM 11-2 which can store measurement data (sensor data) and the like. The CPU 11 is a central processing unit which controls the entire operations of the moisture measuring apparatus 1 in accordance with the program. A temperature table T1, a humidity table T2, and a soil table T3, which are described later, are stored in the RAM 11-2. The power supply section 12 includes a power battery and is a power source control circuit which converts the output of the battery into prescribed voltage and supplies the voltage to each section.

Also, the moisture measuring apparatus 1 includes a temperature sensor 14 which measures an outside air temperature as plant nurturing environment, and a humidity sensor 15 which measures outside air humidity as plant nurturing environment, in addition to a soil moisture amount sensor 13 which measures the amount of moisture (humidity) in the soil in the flower pot 2, as various sensors to measure plant nurturing environment. The soil moisture amount sensor 13 is a sensor to measure the amount of moisture as a state of moisture in soil based on the electric resistance value between the two sensor electrodes 1a described above. The CPU 11 judges the mounting state of the moisture measuring apparatus 1 in soil (whether or not the current state is a state where a gap has been occurred between the sensor electrode 1a and soil) based on change in the moisture state (moisture amount) measured by the soil moisture amount sensor 13 in a predetermined amount of time. A switch section 16 is a key operation section which includes a power on/off key and the like. A radio communication section 17 is a communication section which carries out general-purpose protocol communication between the moisture measuring apparatus 1 and the information collection terminal 3 with the use of the wireless LAN (WLAN) and standard Internet protocol (TCP/IP).

Figure 3A:
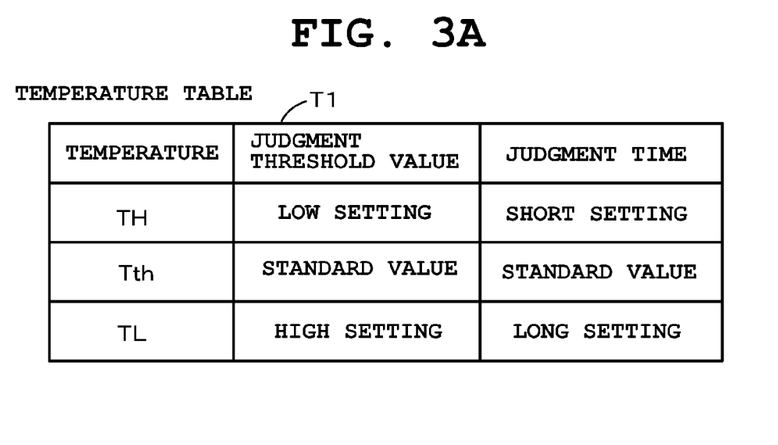
FIGS. 3A to 3C are diagrams to describe a temperature table T1, a humidity table T2, and a soil table T3 in a RAM 11-2.
Figure 3B:
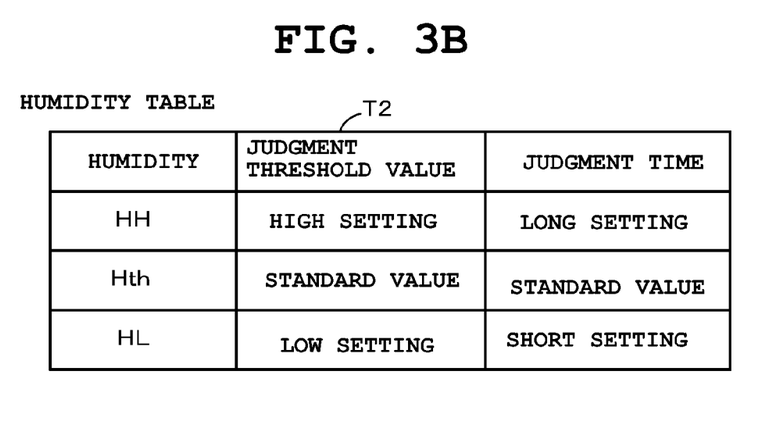
Figure 3C:
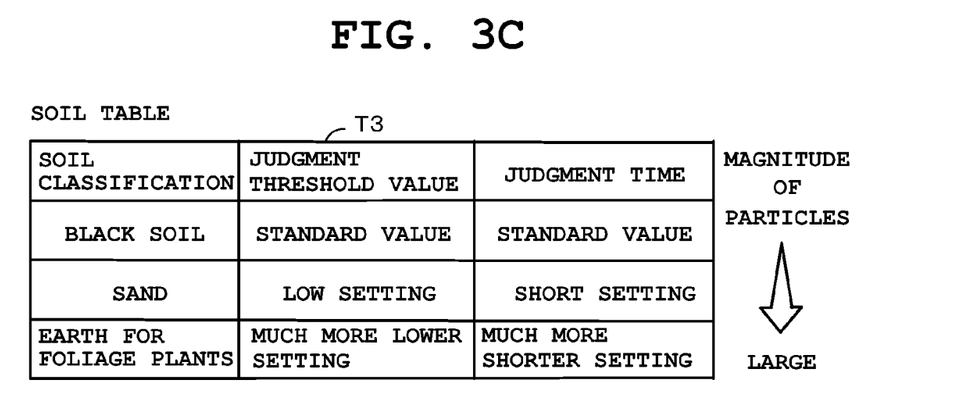

FIG. 3 is a diagram to describe the temperature table T1, the humidity table T2, and the soil table T3 in the RAM 11-2. The temperature table T1, the humidity table T2, and the soil table T3 are tables that are used when the CPU 11 judges the mounting state of the moisture measuring apparatus 1 in soil (whether or not the current state is a state where a gap has been occurred between the sensor electrode 1a and soil). That is, the contact area between the sensor electrode 1a and soil is substantially reduced when there is a gap between the sensor electrode 1a and soil, which impedes exact measurements. Accordingly, in the embodiment of the present invention, the CPU 11 judges the mounting state of the moisture measuring apparatus 1. At the time of this judgment, the CPU 11 refers to the contents of the aforementioned temperature table T1, the humidity table T2, and the soil table T3.

Figure 4:
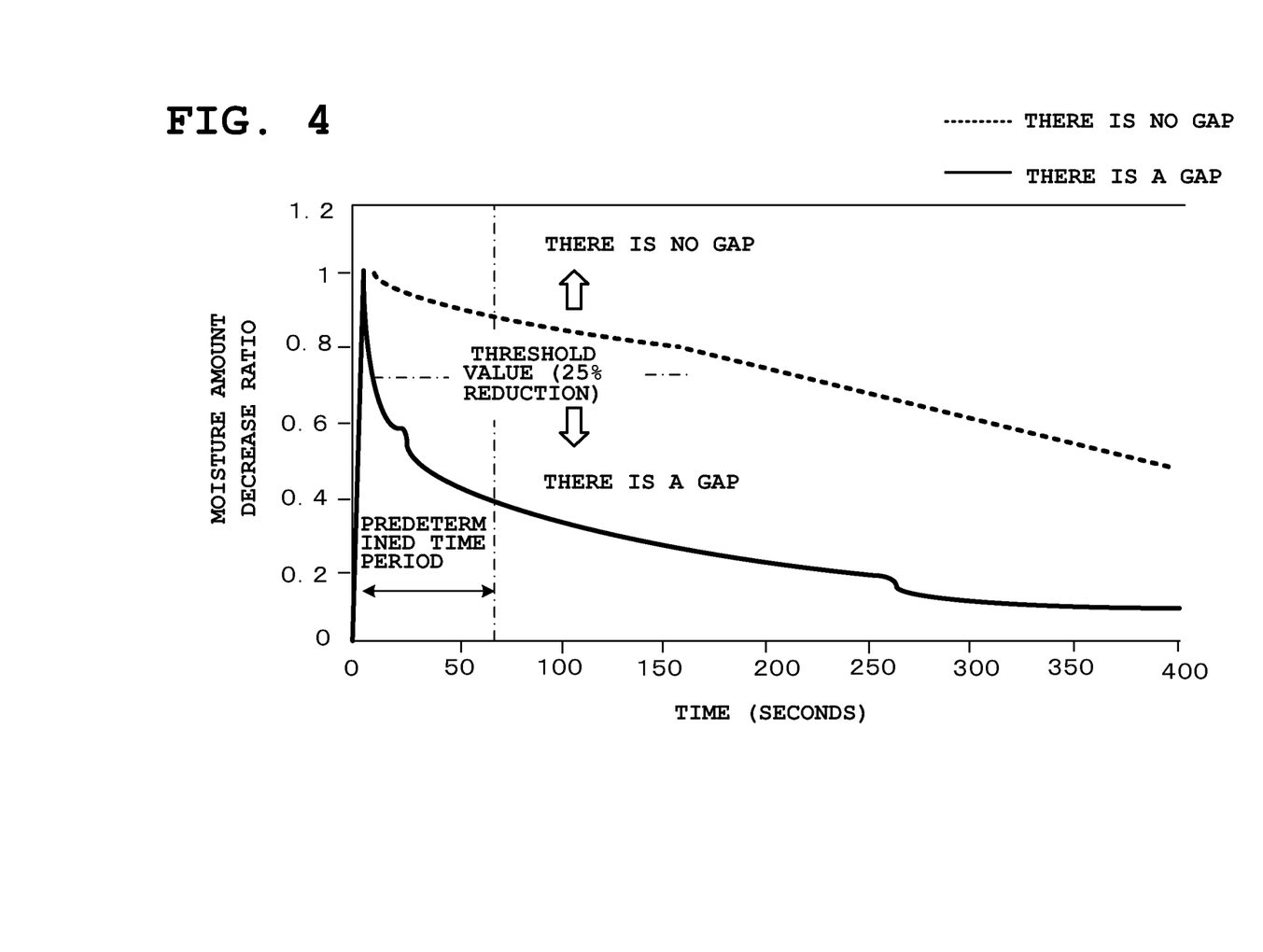
FIG. 4 is a diagram illustrating a state of change in a moisture amount decrease ratio in a case where there is no gap between a sensor electrode 1a and soil immediately after the start of watering, and in a case where there is a gap between the sensor electrode 1a and the soil immediately after the start of watering.

FIG. 4 is a diagram illustrating a state of change in a moisture amount decrease ratio in a case where there is no gap between the sensor electrode 1a and soil immediately after the start of watering, and in a case where there is a gap between the sensor electrode 1a and the soil immediately after the start of watering. In the diagram, the horizontal axis represents time (unit, second), and the vertical axis represents the moisture amount decrease ratio. The curve in a dotted line represents the change curve of the moisture amount in the case there is no gap between the sensor electrode 1a and the soil. The curve in a solid line represents the change curve of the moisture amount in the case there is a gap between the sensor electrode 1a and the soil. When there is no gap between the sensor electrode 1a and the soil, the contact between the sensor electrode 1a and the soil is sufficiently secured, whereby the moisture amount decrease ratio is moderately changed, as illustrated by the curve in the dotted line in the diagram. In the period of "zero seconds to 400 seconds" immediately after the start of watering, the decrease ratio reaches approximately "1 to 0.5", which is the reduction of approximately 50%.

In contrast, when there is a gap between the sensor electrode 1a and the soil, the gap between the sensor electrode 1a and the soil is filled with water immediately after the start of watering to the soil, whereby the sensor electrode 1a is brought into contact with the water. However, after a while, the water is infiltrated into the soil from the gap, and there occurs the gap between the sensor electrode 1a and the soil again, so that the moisture amount decrease ratio is rapidly changed, as illustrated by the curve in the solid line in the diagram. In the period of "zero seconds to 400 seconds" immediately after the start of watering, the moisture amount decrease ratio reaches approximately "1 to 0.1", which is the reduction of approximately 90%.

In view of this, in the embodiment of the present invention, the CPU 11 judges the presence or absence of a gap based on a moisture amount decrease ratio. That is, the CPU 11 acquires a moisture amount decrease ratio (a ratio of the maximum value to the minimum value) based on a moisture amount (maximum value) immediately after the start of watering and a moisture amount (minimum value) after a predetermined amount of time (60 seconds) from the start of watering. Then, the CPU 11 judges whether or not there is a gap between the sensor electrode 1a and the soil by comparing the moisture amount decrease ratio with a predetermined threshold value. In the illustrated example, in a case where a moisture amount decrease ratio immediately after the start of watering is "100%", a moisture amount decrease ratio after a predetermined amount of time (60 seconds) is 25%, whose reduction level serves as a judgment threshold value. Here, when the moisture amount decrease ratio is higher than the judgment threshold value, the CPU 11 judges that there is a gap between the sensor electrode 1a and the soil. When the moisture amount decrease ratio is lower than the judgment threshold value, the CPU 11 judges that there is no gap between the sensor electrode 1a and the soil.

The time and the threshold value that are used in this judgment are affected by the present nurturing environment (temperature, humidity, and soil classification). Accordingly, the CPU 11 determines a judgment threshold value and a judgment time suitable for the present nurturing environment, with reference to the temperature table T1, the humidity table T2, and the soil table T3. The temperature table T1 is configured to store "judgment threshold value" and "judgment time" corresponding to "temperature". The amount of moisture evaporation is affected by temperatures, so that "low setting", "standard value (ideal value: for example, 25% reduction)", and "high setting" for "judgment threshold value", and "short setting", "standard value (ideal value: for example, 60 seconds)", and "long setting" for "judgment time" are stored corresponding to "TH (high)", "Tth (ideal temperature range for example, 10 to 25 degrees)", and "TL (low)" for "temperatures".

The humidity table T2 is configured to store "judgment threshold value" and "judgment time" corresponding to "humidity". The amount of moisture evaporation is affected by humidity, so that "high setting", "standard value (ideal value: for example, 25% reduction)", and "low setting" for "judgment threshold value", and "long setting", "standard value (ideal value a for example, 60 seconds)", and "short setting" for "judgment time" are stored corresponding to "TH (high)", "Tth (ideal humidity range: for example, 45% to 60%)", and "TL (low)" for "humidity".

The soil table T3 is configured to store "judgment threshold value" and "judgment time" corresponding to "soil classification". The influence with respect to soil classification is attributed to the magnitude of particles of earth (drainage and infiltration), and the magnitude of particles is expressed in an inequality of "black soil"<"sand"<"earth for foliage plants", so that "standard value (ideal value: for example, 25% reduction)", "low setting", and "much more lower setting" for "judgment threshold value", and "standard value (ideal values for example, 60 seconds)", "short setting", and "much more shorter setting" for "judgment time" are stored corresponding to "black soil" "sand", and "earth for foliage plants" for "soil classification".

Figure 5:
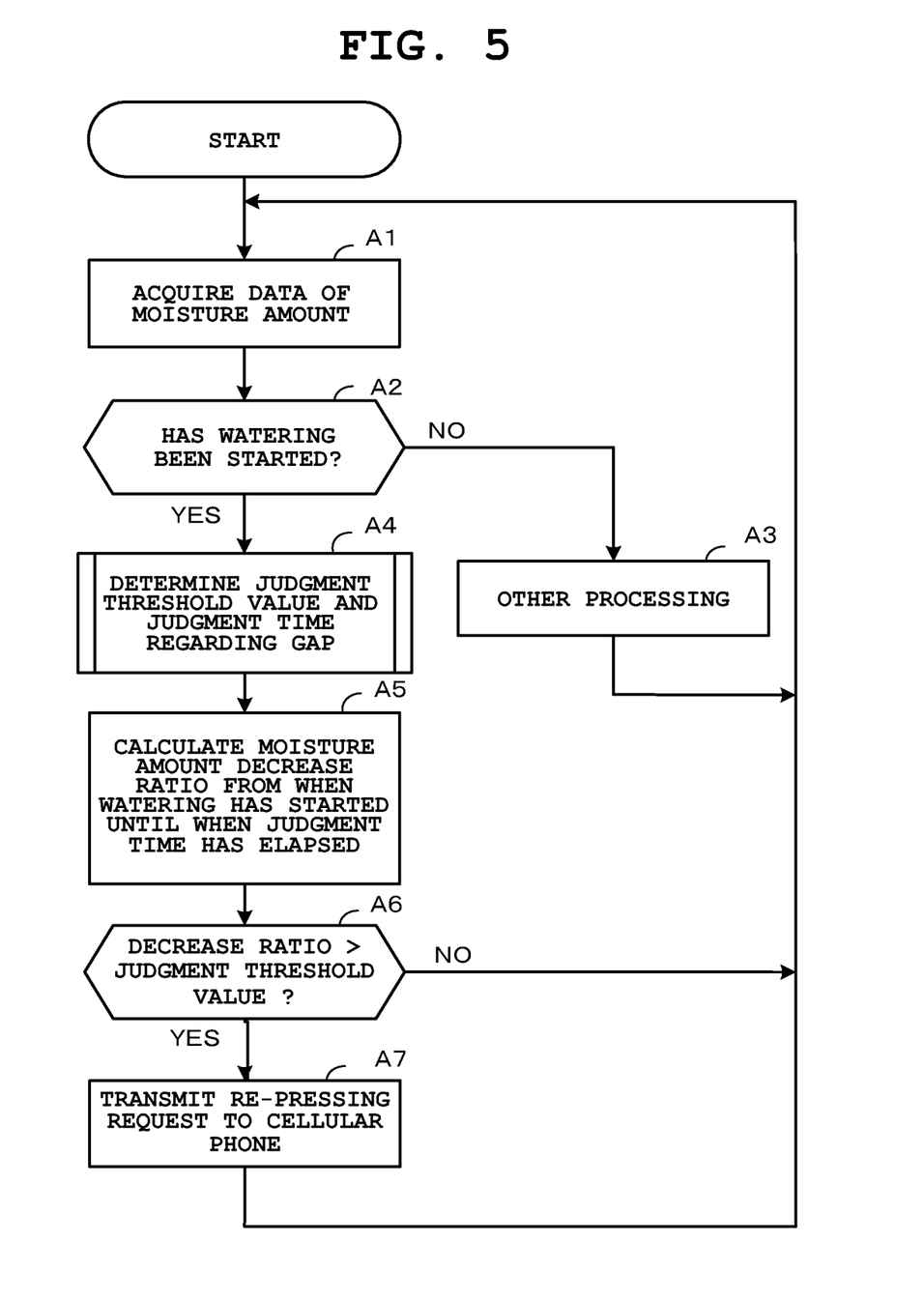
FIG. 5 is a flowchart outlining the operation of a characteristic portion of the embodiment from among all of the operations of the moisture measuring apparatus 1.
Figure 6:
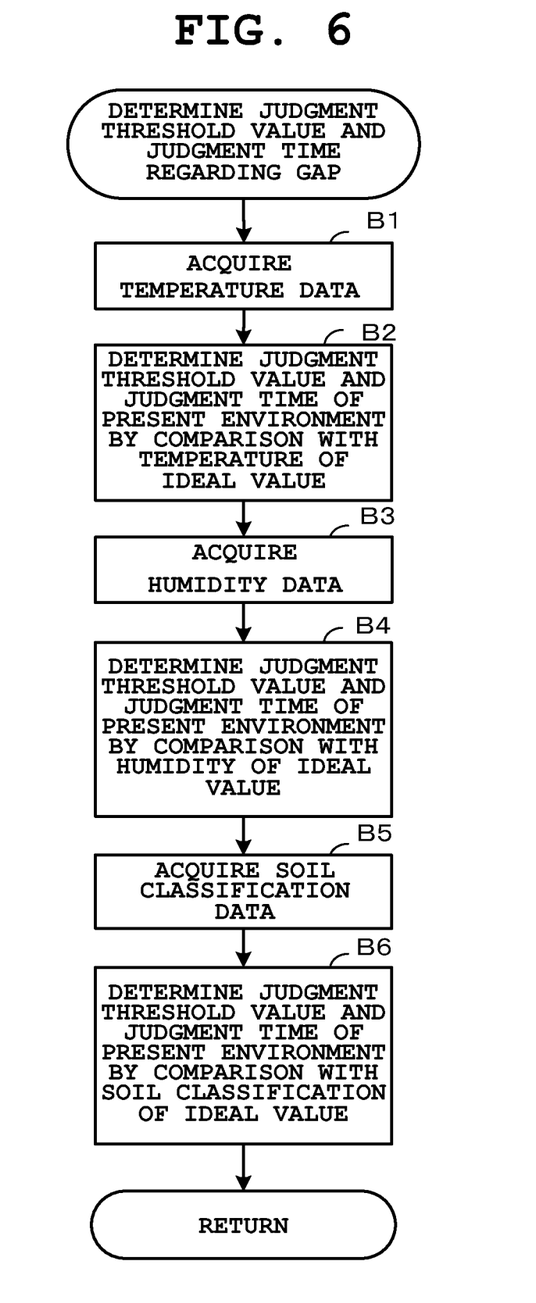
FIG. 6 is a flowchart to describe in detail processing (Step A4 in FIG. 5) for determining a judgment threshold value and a judgment time which are used to judge the presence or absence of a gap, based on the present nurturing environment.

Next, the operational concept of the moisture measuring apparatus 1 according to the embodiment of the present invention win be described referring to flowcharts illustrated in FIGS. 5 and 6. Here, each function described in the flowcharts is stored in a readable program code format, and operations based on these program codes are sequentially performed. Also, operations based on the above-described program codes transmitted over a transmission medium such as a network can also be sequentially performed. That is, the unique operations of the present embodiment can be performed using programs and data supplied from an outside source over a transmission medium, in addition to a recording medium.

FIG. 5 is a flowchart outlining the operation of a characteristic portion of the embodiment from among all of the operations of the moisture measuring apparatus 1, which is started upon power-on. The moisture measuring apparatus 1 is thrust into soil which is a measurement target object. In a state, where the two sensor electrodes 1*a* are fully buried in the soil, the CPU 11 acquires data regarding the amount of moisture in the soil, which is measured based on an electric resistance value between the two sensor electrodes 1*a* by the soil moisture amount sensor 13 (Step A1). Subsequently, the CPU 11 judges whether it is immediately after the start of watering based on the magnitude of the value of the moisture amount data (Step A2). In this case, with regards to whether it is immediately after the start of watering, the CPU 11 judges whether the value of the measured moisture amount data is equal to or higher than a predetermined threshold value. Alternatively, the CPU 11 compares the previous measurement result with the present measurement result and judges whether it is immediately after the start of watering, based on whether the moisture amount has rapidly increased. However, the method of the judgment may be arbitrarily determined.

Here, when judged that it is not immediately after the start of watering (Step A2, NO), the CPU 11 allows the RAN 11-2 to store the moisture amount data measured by the soil moisture amount sensor 13 as other processing, or carries out processing for transmitting the moisture amount data in the RAM 11-2 to the information collection terminal 3 in response to an access request from the information collection terminal 3 (Step A3). Then, the CPU 11 returns to the aforementioned Step A1 where data regarding the amount of moisture in the soil is acquired. Also, when judged that it is immediately after the start of watering (Step A2, YES), the CPU 11 carries out processing for determining a judgment threshold value and a judgment time which are used to judge the presence or absence of a gap, based on the present nurturing environment (Step A4).

FIG. 6 is a flowchart to describe in detail the processing (Step A4 in FIG. 5) for determining a judgment threshold value and a judgment time which are used to judge the presence or absence of a gap, based on the present nurturing environment. First, the CPU 11 acquires temperature data measured based on the temperature table T1 (Step B1). Subsequently, the CPU 11 refers to the temperature table T1 based on the temperature data, and determines a judgment threshold value and a judgment time corresponding to the present nurturing environment (temperature) by comparing the present nurturing environment (temperature) with the temperature of the ideal value (standard value) (Step B2).

That is, when the present nurturing environment (temperature) is equivalent to the ideal value (standard value), the CPU 11 determines "standard value (ideal value: for example, 25% reduction)" as "judgment threshold value" and determines "standard value (ideal value; for example, 60 seconds)" as "judgment time" Also, when the present nurturing environment is higher than the ideal value (standard value) the CPU 11 determines "low setting" as "judgment threshold value" and determines "short setting" as "judgment time". When the present nurturing environment is lower than the ideal value (standard value), the CPU 11 determines "high setting" as "judgment threshold value" and determines "long setting" as "judgment time".

Next, the CPU 11 acquires humidity data measured based on the humidity table T2 (Step B3). Subsequently, the CPU 11 refers to the humidity table T2 based on the humidity data, and determines a judgment threshold value and a judgment time corresponding to the present nurturing environment (humidity) by comparing the present nurturing environment (humidity) with the humidity of the ideal value (standard value) (Step B4). That is, when the present nurturing environment (humidity) is equivalent to the ideal value (standard value), the CPU 11 determines "standard value (ideal value: for example, 25% reduction)" as "judgment threshold value" and determines "standard value (ideal value: for example, 60 seconds)" as "judgment time". Also, when the present nurturing environment is higher than the ideal value (standard value), the CPU 11 determines "high setting" as "judgment threshold value" and determines "long setting" as "judgment time". When the present nurturing environment is lower than the ideal value (standard value), the CPU 11 determines "low setting" as "judgment threshold value" and determines "short setting" as "judgment time".

Next, the CPU 11 acquires the classification data of the soil (Step B5). In this case, when the classification data of the soil has been inputted and set in advance, the CPU 11 reads out and acquires the data. When the classification data of the soil has not been set in advance, the CPU 11 acquires the classification data of the soil inputted based on a user operation. Subsequently, the CPU 11 refers to the soil table T3 based on the acquired classification data of the soil, and determines a judgment threshold value and a judgment time corresponding to the present nurturing environment (soil classification) by comparing the present nurturing environment (soil classification) with the soil of the ideal value (standard value) (Step B6).

That is, when the present nurturing environment (soil classification) is equivalent to the ideal value (standard value: black soil), the CPU 11 determines "standard value (ideal value: for example, 25% reduction)" as "judgment threshold value" and determines "standard value (ideal value for example, 60 seconds)" as "judgment time". Also, when the soil classification is sand, the CPU 11 determines "low setting" as "judgment threshold value" and determines "short setting" as "judgment time". When the soil classification is the earth for foliage plants, the CPU 11 determines "much more lower setting" as "judgment threshold value" and determines "much more shorter setting" as "judgment time".

When the processing for determining a judgment threshold value and a judgment time suitable for the present nurturing environment is complete (Step A4 in FIG. 5), the CPU 11 calculates the decrease ratio of the moisture amount corresponding to change in the moisture amount occurred in a time period between the start of the watering and the end of the judgment time (Step A5). In this case, the CPU 11 calculates the moisture amount decrease ratio (a ratio of the maximum value to the minimum value) based on the measurement value (maximum value) measured by the soil moisture amount sensor 13 immediately after the start of the watering and the measurement value (minimum value) measured by the soil moisture amount sensor 13 after the elapse of the judgment time. Subsequently, the CPU 11 judges whether or not the calculated ratio is higher than the judgment threshold value by comparing the calculated moisture amount decrease ratio with the judgment threshold value. Then, the CPU 11 determines the mounting state of the moisture measuring apparatus 1 in the soil based on the result (judges whether or not the current state is a state where a gap has been occurred between the sensor electrode 1a and the soil) (Step A6).

Here, when the moisture amount decrease ratio measured this time is equal to or lower than the judgment threshold value (Step A6, NO), the CPU 11 judges that the current state is a normal state where no gap has been occurred between the sensor electrode 1a and the soil, and returns to the aforementioned Step A1 where data regarding the amount of moisture in the soil is acquired. When the moisture amount decrease ratio measured this time is higher than the judgment threshold value (Step A6, YES), the CPU 11 judges that the current state is an unusual state where a gap has been occurred between the sensor electrode 1a and the soil, and proceeds to the next Step A7a. At Step A7, the CPU 11 transmits to the information collection terminal 3 a request to re-insert the moisture measuring apparatus 1 as a warning message (Step A7). Then, the CPU 11 returns to the aforementioned Step A1 where data regarding the amount of moisture in the soil is acquired.

As described above, in the embodiment of the present invention, the moisture measuring apparatus 1 makes a judgment regarding the mounting state of the moisture measuring apparatus 1 in soil (measurement target object) based on the moisture state measured by the soil moisture amount sensor 13, and informs the judgment result. As a result of this configuration, when the body of the apparatus which measures the state of moisture in soil is mounted into soil, the mounting state as to whether the moisture measuring apparatus 1 has been appropriately mounted can be provided to the user, whereby the exact measurement can be expected.

Also, the moisture measuring apparatus 1 acquires change in a moisture state in a predetermined time period based on a result of measurement by the soil moisture amount sensor 13, and thereby judges the mounting state of the moisture measuring apparatus 1 in the soil. As a result of this configuration, more exact judgment can be made, compared with a case where a mounting state is judged based only on a moisture amount measured at certain timing.

Moreover, the moisture measuring apparatus 1 makes a judgment regarding the mounting state of the moisture measuring apparatus 1 based on whether the ratio of the maximum value to the minimum value (moisture amount decrease ratio) in change in a moisture state in a predetermined time period measured by the soil moisture amount sensor 13 is equal to or higher than a predetermined threshold value. When the ratio of the maximum value to the minimum value (moisture amount decrease ratio) is equal to or higher than the predetermined threshold value, the moisture measuring apparatus 1 judges whether the current state is a mounting state where a gap has been occurred between the sensor electrode 1a and the soil. As a result of this configuration, judgment as to the presence or absence of a gap (mounting state) can be made by merely comparing the ratio of the maximum value to the minimum value with the predetermined threshold value, whereby the judgment can be made more steadily and readily.

Furthermore, the moisture measuring apparatus 1 judges whether it is immediately after the start of watering to soil based on the state of moisture in the soil, and makes a judgment regarding the mounting state based on whether or not change in the moisture state measured in a predetermined time period immediately after the start of the watering (the ratio of the maximum value to the minimum value) is equal to or higher than a predetermined threshold value. As a result of this configuration, the mounting state can be judged based on a moisture state which substantially changes from when watering is started until when a predetermined amount of time elapses, whereby the judgment can be made more steadily and readily.

Still further, the moisture measuring apparatus 1 refers to the temperature table T1 based on temperature measured by the temperature sensor 14 and makes a judgment regarding the mounting state based on a judgment standard corresponding to the temperature. As a result of this configuration, the judgment standard can be changed corresponding to temperature that affects the amount of moisture evaporation, which makes it possible to respond to change in a measurement environment (temperature) and provide more steady judgment.

Yet still further, the moisture measuring apparatus 1 refers to the humidity table T2 based on humidity measured by the humidity sensor 15 and makes a judgment regarding the mounting state based on a judgment standard corresponding to the humidity. As a result of this configuration, the judgment standard can be changed corresponding to humidity which affects the amount of moisture evaporation, which makes it possible to respond to change in a measurement environment (humidity) and provide more steady judgment.

Yet still further, the moisture measuring apparatus 1 refers to the soil table T3 based on soil classification serving as a measurement environment, and judges the mounting state based on a judgment standard corresponding to the soil classification. As a result of this configuration, the judgment standard can be changed corresponding to soil classification which affects the magnitude of particles of soil (drainage and infiltration), which makes it possible to respond to change in a measurement environment (soil classification) and provide more steady judgment.

The mounting state of the moisture measuring apparatus 1 is transmitted to the information collection terminal 3, so that, even when the user is away from the moisture measuring apparatus 1, he or she can check the mounting state of the moisture measuring apparatus 1, and can immediately respond to the situation of the moisture measuring apparatus 1.

In the aforementioned embodiment of the present invention, the mounting state of the moisture measuring apparatus 1 is transmitted to the information collection terminal 3. However, a notification sound section which emits an alarm sound or a display section which displays a blinking display and messages may be provided for the moisture measuring apparatus 1. In this case, if it is immediately after the start of watering, the user is near the moisture measuring apparatus 1 and therefore the mounting state of the moisture measuring apparatus 1 can be informed to the user.

Also, in the aforementioned embodiment of the present invention, soil has been exemplified as the measurement target object. However, perlite for gardening and other water retention members may be applied in place of the soil.

Moreover, in the aforementioned embodiment of the present invention, the amount of moisture has been exemplified as the state of moisture in soil. However, the moisture content ratio may be applied. Furthermore, in the aforementioned embodiment, the mounting state of the moisture measuring apparatus 1 is judged based on a result of measurement by the soil moisture amount sensor 13. However, in the case of soil other than black soil, the mounting state may be judged based on a combination of a result of measurement by the soil moisture amount sensor 13 and a result of measurement by another sensor (for example, a pressure sensor). Still further, in the aforementioned embodiment, the determination of a judgment threshold value and a judgment time regarding a gap is made based on temperature data, humidity data, and soil classification data. However, the determination may be made based only on one of temperature data, humidity data, and soil classification data or a combination of the two out of these pieces of data. In addition, the determination of a judgment threshold value and a judgment time regarding a gap may be made based on data other than the aforementioned three pieces of data.

Still further, the "devices" or the "sections" described in the above-described embodiment are not required to be in a single housing and may be separated into a plurality of housings by function. In addition, the steps in the above-described flowcharts are not required to be processed in time-series, and may be processed in parallel, or individually and independently.

While the present invention has been described with reference to the preferred embodiments, it is intended that the invention be not limited by any of the details of the description therein but includes all the embodiments which fall within the scope of the appended claims.

What is claimed is:

1. A moisture measuring apparatus comprising:
a case;
a sensor connected to the case and insertable into a measurement target object; and
a processor which receives a signal from the sensor and is configured to perform functions including:
measuring a state of moisture in the measurement target object based on the signal received from the sensor;
determining whether a mounting state of the sensor in the measurement target object is appropriate, based on the measured state of moisture; and
outputting a result of the determination.

2. The moisture measuring apparatus according to claim 1, wherein the processor determines whether the mounting state is appropriate based on a change in the measured state of moisture in a predetermined time period.

3. The moisture measuring apparatus according to claim 2, wherein the processor determines whether the mounting state is appropriate based on whether or not a ratio of a maximum value to a minimum value in the change in the measured state of moisture is equal to or higher than a predetermined threshold value.

4. The moisture measuring apparatus according to claim 3, wherein the functions performed by the processor further include:
judging whether a present moment is immediately after a start of watering to soil, as the measurement target object, based on the measured state of moisture,
wherein the processor determines whether the mounting state is appropriate based on whether or not the ratio of the maximum value to the minimum value in the predetermined time period immediately after the start of the watering is equal to or higher than the predetermined threshold value.

5. The moisture measuring apparatus according to claim 1, further comprising:
memory which stores a temperature determination standard,
wherein the processor obtains a temperature measurement and determines whether the mounting state is appropriate with reference to the temperature determination standard based on the temperature measurement.

6. The moisture measuring apparatus according to claim 1, further comprising:
memory which stores a humidity determination standard,
wherein the processor obtains a humidity measurement and determines whether the mounting state is appropriate with reference to the humidity determination standard based on the humidity measurement.

7. The moisture measuring apparatus according to claim 1, further comprising:
a memory which stores a soil determination standard,
wherein the processor determines whether the mounting state is appropriate with reference to the soil determination standard based on a soil classification of a soil which is the measurement target object.

8. The moisture measuring apparatus according to claim 1, wherein the processor outputs the result of the determination by transmitting the result to a terminal to be notified.

9. The moisture measuring apparatus according to claim 1, further comprising:
an output device
wherein the processor outputs the result of the determination via the output device.

10. The moisture measuring apparatus according to claim 1, wherein the processor determines whether the mounting state is appropriate by determining whether a gap exists between the sensor and the measurement target object;
 wherein if the processor determines that a gap exists, the processor determines that the mounting state is not appropriate, and
 wherein if the processor determines that a gap does not exist, the processor determines that the mounting state is appropriate.

11. A non-transitory computer-readable storage medium having stored thereon a program that is executable by a computer of a moisture measuring apparatus that includes a case, a sensor connected to the case and insertable into a measurement target object, and the computer, which receives a signal from the sensor, the program being executable by the computer to perform functions comprising:
 measuring a state of moisture in the measurement target object based on the signal received from the sensor;
 determining whether a mounting state of the sensor in the measurement target object is appropriate, based on the measured moisture state; and
 outputting a result of the determination result.

* * * * *

UNITED STATES PATENT AND TRADEMARK OFFICE
CERTIFICATE OF CORRECTION

| | | |
|---|---|---|
| PATENT NO. | : 9,513,271 B2 | Page 1 of 1 |
| APPLICATION NO. | : 13/928184 | |
| DATED | : December 6, 2016 | |
| INVENTOR(S) | : Ryo Okumura | |

It is certified that error appears in the above-identified patent and that said Letters Patent is hereby corrected as shown below:

In the Claims

Column 10, Line 38, before "memory" insert --a--.

Column 10, Line 46, before "memory" insert --a--.

Column 11, Line 21, delete "determination result" and insert --determination--.

Signed and Sealed this
Twenty-eighth Day of February, 2017

Michelle K. Lee
*Director of the United States Patent and Trademark Office*